United States Patent
Wilson et al.

(10) Patent No.: US 11,371,983 B2
(45) Date of Patent: Jun. 28, 2022

(54) VACUUM-ASSISTED PLASMA SEPARATION

(71) Applicant: Siemens Healthcare Diagnostics Inc., Tarrytown, NY (US)

(72) Inventors: Michael S. Wilson, Waltham, MA (US); Jay Li, Franklin, MA (US); Kenneth P. Galano, Wrentham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/226,464

(22) Filed: Apr. 9, 2021

(65) Prior Publication Data

US 2021/0231642 A1      Jul. 29, 2021

Related U.S. Application Data

(62) Division of application No. 15/329,795, filed as application No. PCT/US2015/042838 on Jul. 30, 2015, now Pat. No. 10,989,706.

(60) Provisional application No. 62/031,908, filed on Aug. 1, 2014.

(51) Int. Cl.
    *G01N 33/49* (2006.01)
(52) U.S. Cl.
    CPC .................. *G01N 33/491* (2013.01)
(58) Field of Classification Search
    CPC .................................................. G01N 33/491
    USPC .............................................................. 435/2
    See application file for complete search history.

(56) References Cited

U.S. PATENT DOCUMENTS

| 4,872,988 A | 10/1989 | Culkin |
| 5,147,606 A | 9/1992 | Charlton et al. |
| 7,927,810 B2 | 4/2011 | Togawa et al. |
| 9,182,326 B2 | 11/2015 | Kurowski et al. |
| 2008/0305008 A1 | 12/2008 | Hyland et al. |
| 2012/0024788 A1 | 2/2012 | Kelso et al. |
| 2012/0145619 A1 | 6/2012 | Urdahl et al. |
| 2012/0156765 A1 | 6/2012 | Wimberger-Friedl et al. |
| 2012/0220047 A1 | 8/2012 | Seifried et al. |
| 2012/0275955 A1 | 11/2012 | Haghgooie |
| 2013/0341265 A1 | 12/2013 | Grolla |

FOREIGN PATENT DOCUMENTS

| CA | 2475348 A1 | 8/2003 |
| EP | 0785430 A1 | 7/1997 |
| WO | 2007000986 A1 | 1/2007 |
| WO | 2012062651 A1 | 5/2012 |
| WO | 2012149126 A1 | 11/2012 |
| WO | 2014023756 A1 | 2/2014 |
| WO | 2014024066 A1 | 2/2014 |

OTHER PUBLICATIONS

Office Action of European Application No. 15826556.1 dated Feb. 8, 2021.

(Continued)

*Primary Examiner* — Jennifer M. H. Tichy

(57) ABSTRACT

A plasma separation system and process for providing filtered plasma from a blood sample is described. The system may include a blood separation well having a separation membrane for filtering the blood sample. The filtering process may be aided by the use of a negative or positive pressure source attached to the plasma separation system.

16 Claims, 6 Drawing Sheets

(56) References Cited

OTHER PUBLICATIONS

Office Action of Canadian Application No. 2,956,710 dated Jul. 2, 2020.
European Search Report and Written Opinion of European Application No. 15826556.1 dated Jun. 23, 2017.
International Search Report and Written Opinion of International Application No. PCT/US2015/042838 dated Oct. 26, 2015.
Nabaliyan, et al.; "Membrane-based plasma collection device for point-of-care diagnosis of HIV," 2011, Journal of Virological Methods 173, pp. 37-42.
Becker, et al.; "Highly Efficient on-Chip Plasma/Serum Generation for Disposable Point-of-Care Devices," Oct. 2010, 14th International Conference on Miniaturized Systems for Chemistry and Life Sciences, pp. 133-135.
Pall, Vivid Plasma Separation Membrane, Available online at: shop.pall.com/us/en/medical/advanced-materials/gas-filtration/cytosep-membrane-zidgri78lgn; Accessed Aug. 3, 2018.

VACUUM-ASSISTED PLASMA SEPARATION

CROSS REFERENCE TO RELATED APPLICATIONS/INCORPORATION BY REFERENCE

The present patent application is a divisional of U.S. Ser. No. 15/329,795, filed on Jan. 27, 2017; which is a national stage entry from the Patent Cooperation Treaty Application identified by serial number PCT/US2015/042838, publication number, WO 2016/019113, titled "Vacuum-Assisted Plasma Separation", filed on Jul. 30, 2015; which claims benefit under 35 USC § 119(e) of U.S. Provisional Application No. 62/031,908, filed Aug. 1, 2014. The entire contents of the above-referenced patent applications are hereby expressly incorporated herein by reference.

BACKGROUND

Plasma, rather than whole blood, is generally the preferred sample for many clinical diagnostic tests. For example, in HIV viral load detection, plasma is separated from whole blood as hemoglobin and other hemolysis products may interfere with detection of viral RNA. As hemoglobin and other hemolysis products may interfere with assay results, plasma may need to be non-hemolyzed.

Within the industry, plasma is usually obtained by centrifuging whole blood separating red blood cells from plasma. The centrifuging process, however, may be slow and require large powered instrumentation. Additionally, once the centrifugation process has begun, the instrument is unavailable for use by another operator until completion of the process.

Progress within the medical industry has been in the development of point-of-care systems to provide rapid and portable care. Because of time restraints, size of equipment, and one-operator use, centrifugation is generally impractical for use in such point-of-care diagnostic instruments. Other separation methods including laminar-flow filtration or capillary-action based processes, however, are also expensive, complex, slow, require large volumes of blood, or may lead to unacceptable levels of hemolysis.

BRIEF DESCRIPTION OF THE SEVERAL VIEWS OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, not every component may be labeled in every drawing.

DETAILED DESCRIPTION

Figure 1:
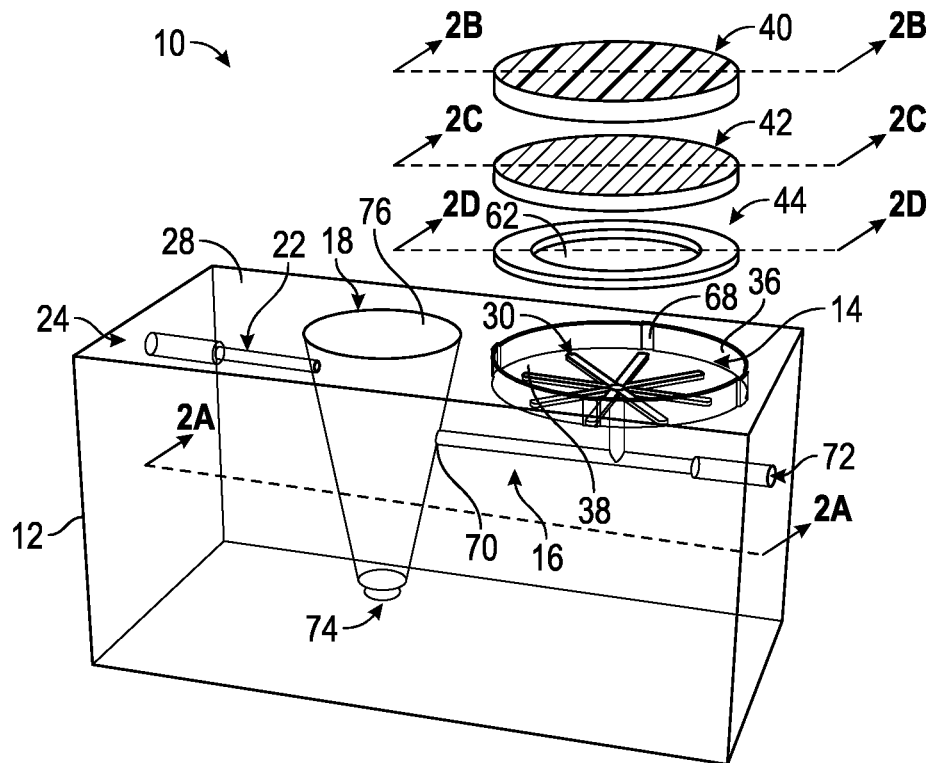
FIG. 1 is an exploded perspective view of an exemplary plasma separation system in accordance with the present disclosure.

Before explaining at least one embodiment of the disclosure in detail, it is to be understood that the disclosure is not limited in its application to the details of construction, experiments, exemplary data, and/or the arrangement of the components set forth in the following description or illustrated in the drawings unless otherwise noted.

The disclosure is capable of other embodiments or of being practiced or carried out in various ways. Also, it is to be understood that the phraseology and terminology employed herein is for purposes of description, and should not be regarded as limiting.

The following detailed description refers to the accompanying drawings. The same reference numbers in different drawings may identify the same or similar elements.

As used in the description herein, the terms "comprises," "comprising," "includes," "including," "has," "having," or any other variations thereof, are intended to cover a non-exclusive inclusion. For example, unless otherwise noted, a process, method, article, or apparatus that comprises a list of elements is not necessarily limited to only those elements, but may also include other elements not expressly listed or inherent to such process, method, article, or apparatus.

Further, unless expressly stated to the contrary, "or" refers to an inclusive and not to an exclusive "or". For example, a condition A or B is satisfied by one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more, and the singular also includes the plural unless it is obvious that it is meant otherwise. Further, use of the term "plurality" is meant to convey "more than one" unless expressly stated to the contrary.

As used herein, any reference to "one embodiment," "an embodiment," "some embodiments," "one example," "for example," or "an example" means that a particular element, feature, structure or characteristic described in connection with the embodiment is included in at least one embodiment.

The appearance of the phrase "in some embodiments" or "one example" in various places in the specification is not necessarily all referring to the same embodiment, for example.

Referring now to the Figures, and in particular to FIG. 1, shown therein and designated by reference numeral 10 is an exemplary plasma separation system 10 in accordance with the present disclosure. Generally, the plasma separation system 10 may provide separation of plasma from blood using a vacuum force, and without using centrifugation or laminar-flow filtration based filtration processes. The separation of plasma from blood may be with minimal hemolysis and within a relatively short amount of time (e.g., 10-90 seconds) as compared to processes used currently within the industry. In some embodiments, the plasma may be further used in one or more point-of-care assays.

The plasma separation system 10 may include a housing 12 supporting or encompassing a blood separation well 14 connected via a first channel 16 to a plasma collection vessel 18. The housing 12 supports or encompasses a second channel 22 connecting the plasma collection vessel 18 to an outlet port 24 downstream of the plasma collection vessel 18. The plasma separation system 10 may also include a negative pressure source 26 that can be attached to the outlet port 24. In this instance, the outlet port 24 can be configured to allow for the negative pressure source 26 to be attached thereto assist in enabling the operation of the plasma separation system 10.

Generally, in the plasma separation system 10, blood may be added to the blood separation well 14. Negative pressure (e.g., vacuum pressure) may be applied by the negative pressure source 26 to the outlet port 24, which also causes a vacuum to form in the blood separation well 14. Using a combination of capillary action and negative pressure, plasma may be separated from the blood. The magnitude of the negative pressure may be controlled to prevent hemolysis and/or leakage of cellular material. The separated plasma may be collected in the plasma collection vessel 18.

In some embodiments, the plasma separation system 10 may be a single-use system. Alternatively, one or more components of the plasma separation system 10 may be disposable such that the plasma separation system 10 may be a multi-use system. For example, in some embodiments, after a first blood sample is separated, one or more channels 16 and 22 may be lined such that the plasma collection vessel 18 and components of the blood separation well 14 may be removed, disposed of, and replaced for use with a second blood sample.

The housing 12 may be formed of materials including, but not limited to, glass, plastic, and/or the like. The shape and size of the housing 12 may be dependent on shape and/or size of the blood separation well 14, channels 16 and 22, and/or the plasma collection vessel 18. The housing 12 that is shown in FIG. 1 is a unitary integral device that is shaped to form the blood separation well 14, channels 16 and 22 and the plasma collection vessel 18. It should be understood that the housing 12 can be constructed of separate components which are connected together so that the blood separation well 14, channels 16 and 22 and the plasma collection vessel 18 communicate with each other. Generally, the size of the housing 12 may be minimized and determinate on an amount of plasma that is desired (e.g., 10-20 μL) to be extracted from a blood sample. The housing 12 may include a surface 28.

The blood separation well 14 may be positioned to intersect the surface 28 of the housing 12 such that the surface 28 at least partially surrounds the blood separation well 14. For example, in some embodiments, the blood separation well 14 may include a recess 30 intersecting the surface 28 of the housing 12 as illustrated in FIGS. 1 and 2 and in this instance the surface 28 may form a rim surrounding the recess 30. The recess 30 may include a proximal end 32 and a distal end 34 with a wall 36 spanning the length of the proximal end 32 to the distal end 34. The proximal end 32 may include a capillary surface 38 in which microchannels are formed in the proximal end 32 as discussed in more detail below with respect to FIG. 3.

The plasma separation device 10 may also be provided with a filter 40, a separation membrane 42, and an adhesive member 44. The filter 40, the separation membrane 42 and the adhesive member 44 may be stacked on the capillary surface 38 and disposed within the recess 30 such that the filter 40 is below the surface 28 of the housing 12 and fully disposed within the recess 30. For example, in some embodiments, the adhesive member 44 may be positioned on the capillary surface 38 with the separation membrane 42 and the filter 40 positioned thereon, respectively. In some embodiments, the filter 40 and/or separation membrane 42 may be pressure fit (also known as a "press fit") within the recess 30.

The size and shape of the recess 30 may be dependent on the size and shape of the filter 40, the separation membrane 42, and/or the adhesive member 44. For example, in some embodiments, the size and shape of the recess 30 may be circular as the filter 40, separation membrane 42, and adhesive member 44 are circular. The shape, however, may be any shape including, but not limited to, rectangular, triangular, or any fanciful shape. The volume of the recess 30, including the height and/or length of wall 36 may be dependent on thicknesses and/or the widths of one or more of the filter 40, separation membrane 42, and/or adhesive member 44. Generally, the filter 40, separation membrane 42 and the adhesive member 44 may be positioned within the recess 30 such that each remains between the proximal end 32 and the distal end 34 of the recess 30. Further, although the wall 36 is depicted as a straight wall, it should be understood that in some embodiments, the wall 36 can be stepped.

In some embodiments, one or more additional layers may be positioned on a first side 48 of the filter 40 to hold the filter 40 and separation membrane 42 within the blood separation well 14. For example, in one example, a plastic O-ring may be positioned on the first surface 48 of the filter 40 to hold the filter 40 and separation membrane 42 within the blood separation well 14. In another example, a cap (e.g., plastic formed cap) may be positioned adjacent or proximal to the first side 48 of the filter 40 and span the length of the blood separation well 14. In some embodiments, the cap may be vented to allow for escape of gas to the outside environment. The cap may serve to hold the filter 40 in close proximity to the separation membrane 42. In one example, as blood wicks into the filter 40 during use, the filter 40 may expand in size such that the cap retains the filter 40 within the blood separation well 14. To that end, the filter 40 may expand in the direction of the separation membrane 42 positioning the filter 40 in close proximity or even in contact with the separation membrane 42.

The filter 40 may be formed of one or more layers 46. Each layer 46 may include the first side 48 and a second side 50 generally opposite of the first side 48. Generally, blood is provided onto and contacts the first side 48 of the filter 40 and passes through the layer 46 of the filter 40 such that filtered blood emerges on the second side 50. The filtered blood may include plasma and a portion of red blood cells that managed to pass through the layer 46. Some of the red blood cells will be captured within the layer 46 of the filter 40.

In other words, the filter 40 generally removes a portion of the red blood cells from the blood and also may reduce separation burden of the separation membrane 42. For example, the filter 40 may remove red blood cells (e.g., up to 70% of red blood cells) within the blood sample. The removal of a significant portion of red blood cells may aid the flow of the filtered blood through the separation membrane 42 and also reduce clogging of the separation membrane 42.

Each layer 46 may be formed of materials including, but not limited to, glass fibers, polyester fibers, cellulose fibers, and/or the like. For example, one or more filters 40 may be a commercially available filter under the trade name designations of VF1, VF2 and GFB, manufactured and distributed by Whatman, having a location in Maidstone Kent. For example, in some embodiments, one or more filters 40 may be a 9.5 mm disc of Whatman VF2 glass fiber.

The second side 50 of the filter 40 may be in proximity to or contact the separation membrane 42. Generally, the separation membrane 42 may remove the remaining red blood cells from the filtered blood providing filtered plasma. The filtered plasma may be essentially cell-free in that the filtered plasma includes minimal cellular debris. For example, hemoglobin content with the filtered plasma may be comparable to plasma obtained by centrifuge techniques currently known within the industry.

In some embodiments, the plasma separation system 10 may solely comprise the separation membrane 42 without the use of the filter 40. For example, the blood may be filtered solely through the separation membrane 42 providing filtered plasma using the methods as described herein.

The separation membrane 42 may be formed of one or more layers 52. Each layer 52 may have a first side 54 and a second side 56. Generally, the filtered blood contacts the first side 54 of the separation membrane 42 passing through the layer 52 of the separation membrane such that filtered plasma emerges on the second side 56.

The separation membrane 42 may be formed of materials including, but not limited to, nylon, polysulfone, polycarbonate and/or the like. For example, in some embodiments, the separation membrane 42 may be an ion-tracked etched membrane.

In some embodiments, the separation membrane 42 may be an asymmetric membrane. For example, the separation membrane 42 may be formed having at least a first set of pores and a second set of pores, with the first set of pores and the second set of pores being different sizes. Generally, larger pores may be formed on the first side 54 of the separation membrane 42 and smaller pores may be formed on the second side 56 of the separation membrane 42 such that the filtered blood flows through the larger pores to the small pores. This may reduce blockage of red blood cells within the separation membrane 42.

In some embodiments, one or both of the filter 40 and/or separation membrane 42 may be treated with one or more blocking agents and/or surfactants. Treatment with blocking agents and/or surfactant may enhance analyte recovery and/or plasma separation efficiency. Surfactants may include, but are not limited to, Tween-20, and/or the like.

By treating with one or more blocking agents, the filter 40 and/or separation membrane 42 may be made more or less hydrophilic, more or less hydrophobic, more or less susceptible to protein adsorption, more or less positively charged, more or less negatively charged and/or the like. For example, in some embodiments, the filter 40 and/or separation membrane 42 may be treated with PAMAM dendrimers, Merquat, or other polycations. Blocking agents may include, but are not limited to bovine serum albumin, Seablock, gelatin, and/or the like.

The second surface 56 of the separation membrane 42 may contact the adhesive member 44. In some embodiments, the adhesive member 44 may prevent leakage of blood cells around the perimeter of the separation membrane 42.

Figure 2A:
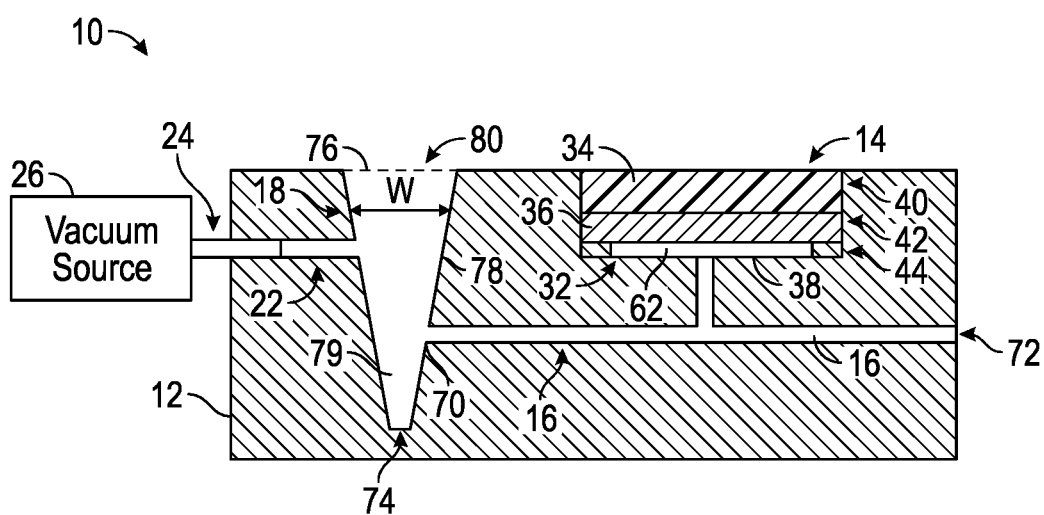
FIG. 2A is a cross-sectional view of the plasma separation system of FIG. 1, taken along the lines 2A-2A in FIG. 1.
Figure 2B:
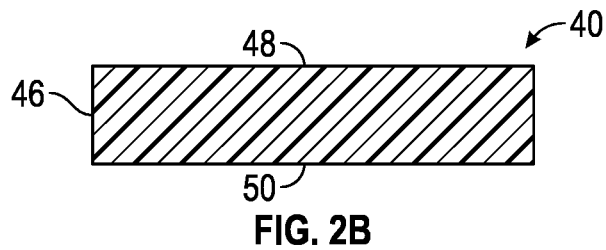
FIG. 2B is a cross-sectional view of an exemplary filter for use in the plasma separation system of FIG. 1, taken along the lines 2B-2B in FIG. 1.
Figure 2C:
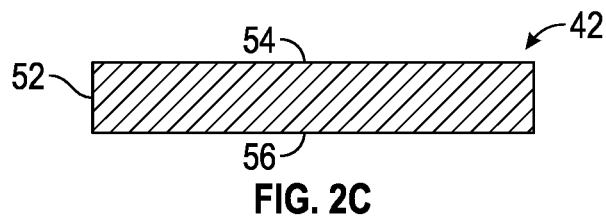
FIG. 2C is a sectional view of an exemplary separation membrane for use in the plasma separation system of FIG. 1, taken along the lines 2C-2C in FIG. 1.
Figure 2D:
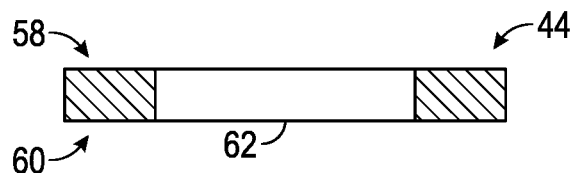
FIG. 2D is a sectional view of an exemplary adhesive member for use in the plasma separation system of FIG. 1, taken along the lines 2D-2D in FIG. 1.

The adhesive member 44 may include a first surface 58 and a second surface 60 with the first surface 58 contacting the second surface 56 of the separation membrane 42 and the second surface 60 adhered to at least a portion of the capillary surface 38 of the recess 30. Generally, the adhesive member 44 aids in holding the separation membrane 42 within the recess 30. To that end, in some embodiments, each surface 58 and 60 of the adhesive member 44 may include an adhesive material. Adhesive material may include, but is not limited to, polyethylene terephthalate (PET) with silicone adhesive, and/or the like. For example, the adhesive member 44 may be a double-sided PET adhesive O-ring as illustrated in FIGS. 2A and 2D. In some embodiments, the adhesive member 44 may be integral to the blood separation well 14 or adhered to the wall 36 of the recess 30.

Size and shape of the adhesive member 44 may be dependent on the size and shape of the separation membrane 42 such that the separation membrane 42 may be positioned within the blood separation well 14 and leakage of filtered blood about edges of the separation membrane 42 may be minimized or eliminated.

The size and shape of the adhesive member 44 may be determined such that the separation membrane 42 is placed in close contact with the capillary surface 38 of the recess 30 of the blood separation well 14 while preventing leakage of blood within the blood separation well 14. In some embodiments, the shape of the adhesive member 44 may include an opening 62. The opening 62 may provide for flow of the filtered plasma to flow from the second surface 56 of the separation membrane 42 to the capillary surface 38 of the recess 30. For example, in some embodiments, the adhesive member 44 may be formed as an O-ring, or any fanciful shape providing a direct opening 62 for flow of filtered plasma from the second surface 56 of the separation membrane 42 to the capillary surface 38 of the recess 30. Additionally, in some embodiments, the material of the adhesive member 44 may be formed of a mesh-type material.

Figure 3:
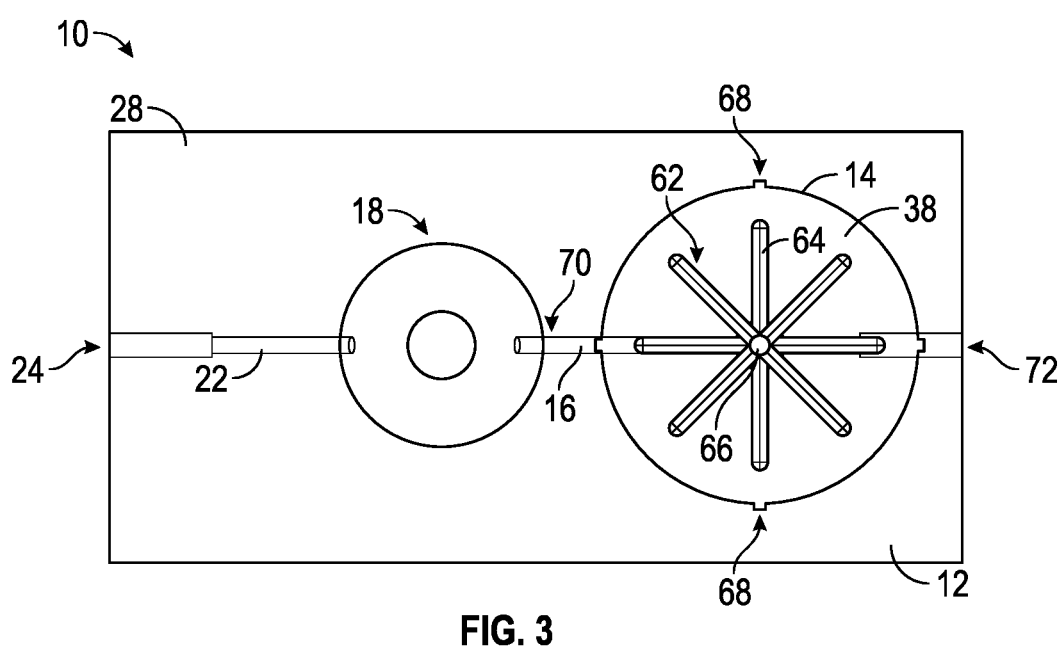
FIG. 3 is a partial top down view of the plasma separation system of FIG. 1 having the filter, the separation membrane, and the adhesive member removed.

Referring to FIGS. 2A and 3, the capillary surface 38 of the recess 30 of the blood separation well 14 may include one or more microchannels 64. Microchannels 64 may encourage capillary flow of the filtered plasma. Microchannels 64 may form any pattern capable of enhancing capillary flow of the filtered plasma through the blood separation well 14. For example, in FIGS. 1 and 3, eight microchannels 64 are used to form a concentric pattern having a plurality of radial microchannels connecting at a central axis 66. Although eight microchannels 64 are illustrated in FIGS. 1 and 3, it should be apparent to one skilled in the art that any number of microchannels 64 may be used so long as such microchannels 64 are positioned within the confines of the capillary surface 38. Additionally, one or more tributaries may be included within the concentric pattern. It should be noted that the capillary surface 38, in some embodiments, may not include microchannels 64 as capillary flow may still occur without such microchannels 64.

In some embodiments, one or more venting channels 68 may be positioned within the recess 30 of the blood separation well 14. For example, in FIGS. 1 and 3, four venting channels 68 are provided within the recess 30 of the blood separation well 14 extending from the capillary surface 38 to the surface 28. Venting channels 68 may provide for venting of gas (e.g., air) within the blood separation well 14. For example, gas entering the filter 40 and/or separation membrane 42 may exit the blood separation well 14 through the one or more venting channels 68.

The filtered plasma may flow from the blood separation well 14 to the channel 16. The channel 16 may include a first outlet 70 connected to the plasma collection vessel 18. In some embodiments, the channel 16 may also include a second outlet 72. Generally, the second outlet 72 may be blocked during operation of the plasma separation system 10 to cause the vacuum force to be directed into the blood separation well via the channel 16. The second outlet 72 may be capable of being selectively opened to provide for removal of any additional filtered blood and/or filtered plasma from within the blood separation well 14 and/or channel 16.

The filtered plasma may flow through the channel 16 and through the first outlet 70 to the plasma collection vessel 18. The plasma collection vessel 18 may have a proximal end 74 and a distal end 76 connected by a tapered wall 78. For example, the width of the plasma collection vessel 18 may increase from the proximal end 74 to the distal end 76. Although the shape of the plasma collection vessel 18 is shown as conical, it should be apparent that the plasma collection vessel 18 may be formed in other shapes (e.g., cylindrical). Generally, the plasma collection vessel 18 may be formed such that the amount of volume where the filtered plasma collects reduces dead volume. For example, the shape of the plasma collection vessel 18 may be formed such that the filtered plasma collects in an area wherein recovery of the filtered plasma by a pipette or other collection means may be maximized (e.g., collection of 10-20 μL of filtered plasma).

Generally, the first outlet 70 may be positioned below the output port 24 and near the proximal end 74 of the plasma collection vessel 18. Collection of filtered plasma may be in a portion 79 positioned below the first outlet 70, e.g., between the first outlet 70 and the proximal end 74 of the plasma collection vessel 18 as illustrated in FIG. 2A.

The plasma collection vessel 18 may include a seal 80. The seal 80 may cover the distal end 76 of the plasma collection vessel 18 so that vacuum force applied to the output port 24 of the channel 22 is directed through the plasma collection vessel 18 and into the channel 16. In some embodiments, the seal 80 may be formed of pierceable material. For example, the seal 80 may be formed of materials capable of being pierced by a pipet tip or similar mechanism for collection of plasma from the plasma collection vessel 18. Such materials may include, but are not limited to, acetate, polyethylene, foil and/or the like.

The plasma collection vessel 18 may be connected to the channel 22. The channel 22 may be positioned above the channel 16, and in proximity to the distal end 76 of the plasma collection vessel 18, e.g., between the channel 16 and the distal end 76. The channel 22 may connect the plasma collection vessel 18 to the negative pressure source 26 via the outlet port 24. In some embodiments, the outlet port 24 of the channel 22 may include a fitted tube or luer connection at which the negative pressure source 26 is connected.

The negative pressure source 26 may be any source capable of providing force between approximately 0.05-2 psi. For example, the negative pressure source 26 may include, but is not limited to, a pump, a syringe pump, a vacuum pump, a suction pump, and/or the like. Generally, the negative pressure source 26 may be capable of being controlled such that plasma may be collected without hemolysis and/or free of cellular material from the blood. For example, by controlling the force of the negative pressure source 26 within the boundaries discussed above, the risks of damage to the plasma may be reduced such that the blood may not hemolyze and/or cells may not deform (i.e., pass through the separation membrane 42).

Control of the negative pressure source 26 may provide for a fixed flow rate and volume. For example, in some embodiments, one or more pressure sensors or monitors may be used to control the negative pressure source 26. In another example, displacement speed of a syringe may control the rate and volume of the negative pressure source 26.

Figure 4:
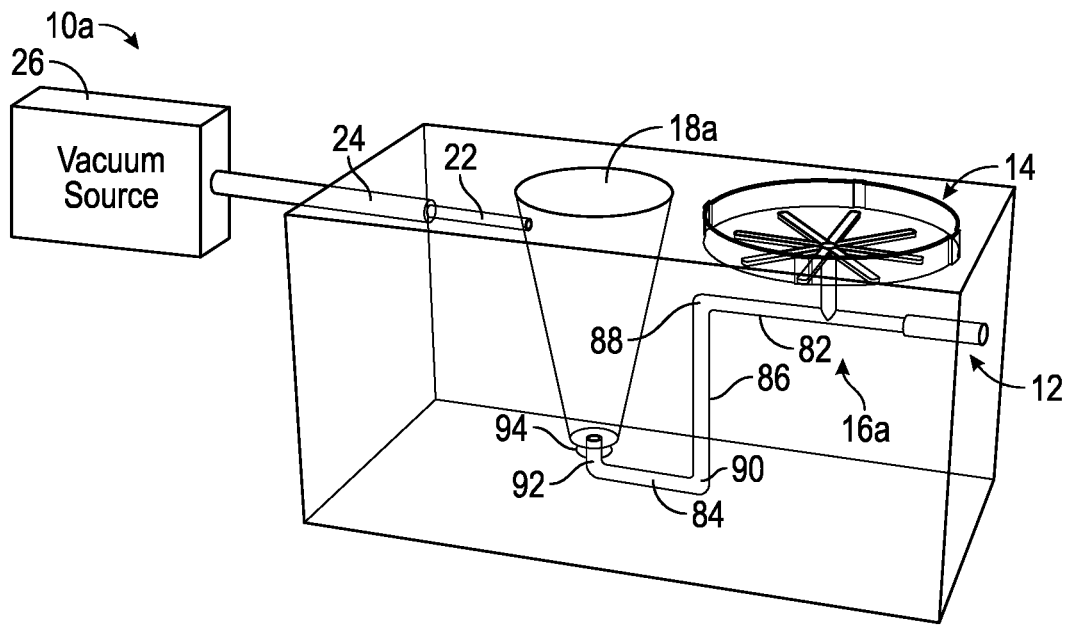
FIG. 4 is a partial perspective view of another version of an exemplary plasma separation system having a channel connected to a proximal end of a plasma collection vessel in accordance with the present disclosure.

FIG. 4 illustrates another exemplary embodiment of a plasma separation system 10a. Similar to the plasma separator system 10 of FIG. 1, the plasma separation system 10a includes the housing 12 supporting or encompassing the blood separation well 14. The blood separation well 14 is connected via a first channel 16a to a plasma collection vessel 18a such that filtered plasma enters the plasma collection vessel 18a from a proximal end 94 of the plasma collection vessel 18a. A second channel 22 connects the plasma collection vessel 18a to an outlet port 24 downstream of the plasma collection vessel 18a. The outlet port 24 may allow for a negative pressure source 26 (e.g., vacuum source) to be attached to the plasma separator system 10a.

The channel 16a may be implemented in a variety of manners such that the channel 16a connects the plasma collection vessel 18a to the proximal end 94 of the plasma collection vessel 18a. For example, the channel 16a may include a variety of linear segments that are interconnected as shown in FIG. 4. In the example depicted in FIG. 4, the channel 16a includes a first portion 82 and a second portion 84 that may be in parallel alignment connected by a third portion 86 extending between the first portion 82 and the second portion 84. In the example shown, the third portion 86 extends normally to the first portion 82 and the second portion 84 and vertically within the housing 12. Although the channel 16a includes corners 88 and 90 formed by intersection of the first portion 82 and the second portion 84 with the third portion 86, it should be noted, the corners 88 may include rounded edges. Additionally, the third portion 86 may be positioned at an angle relative to the first portion 82 and the second portion 84 such that the third portion 86 provides a sloped connection between the first portion 82 and the second portion 84. A fourth portion 92 of the channel 16a may provide an inlet 94 into the proximal end 94 of the plasma collection vessel 18a.

Generally, in the plasma separation system 10a, blood may be added to the blood separation well 14. Vacuum pressure may be applied via the outlet port 24. Using a combination of capillary action and vacuum pressure, plasma may be separated from the blood. The plasma may enter and collect at the proximal end 94 of the plasma collection vessel 18a. The vacuum pressure may be controlled to prevent hemolysis and/or leakage of cellular material.

Figure 5:
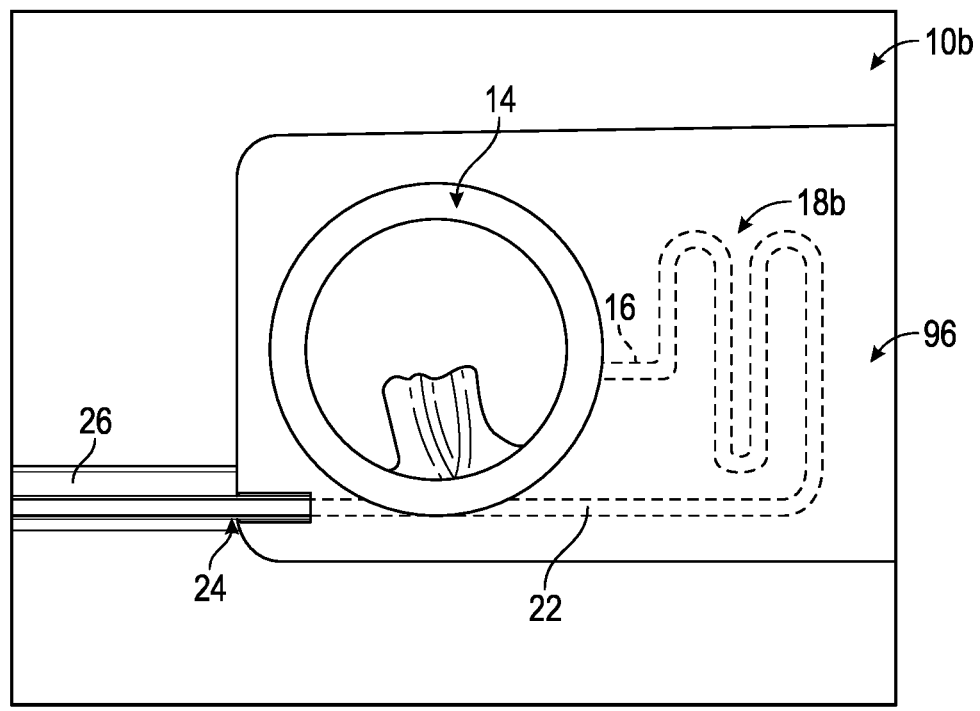
FIG. 5 is a top down view of yet another version of an exemplary plasma separation system having a plasma collection vessel with a serpentine channel in accordance with the present disclosure.

FIG. 5 illustrates another exemplary embodiment of a plasma separation system 10b which is similar in construction to the plasma separation systems 10 and 10a shown in FIGS. 1 and 4 with the exception that plasma separation system 10b includes a plasma collection vessel 18b in the form of a serpentine channel 96, rather than a well. Since the volume of the serpentine may be controlled by the length of the serpentine channel 96, the system 10b can be used to meter the plasma. The serpentine channel 96 can be readily integrated with other standard microfluidic features such as valves and reaction wells for performing quantitative and qualitative assays. The number of curves, the configuration and/or the length of the serpentine channel 96 may be determined based on the assay of interest.

Figure 6:
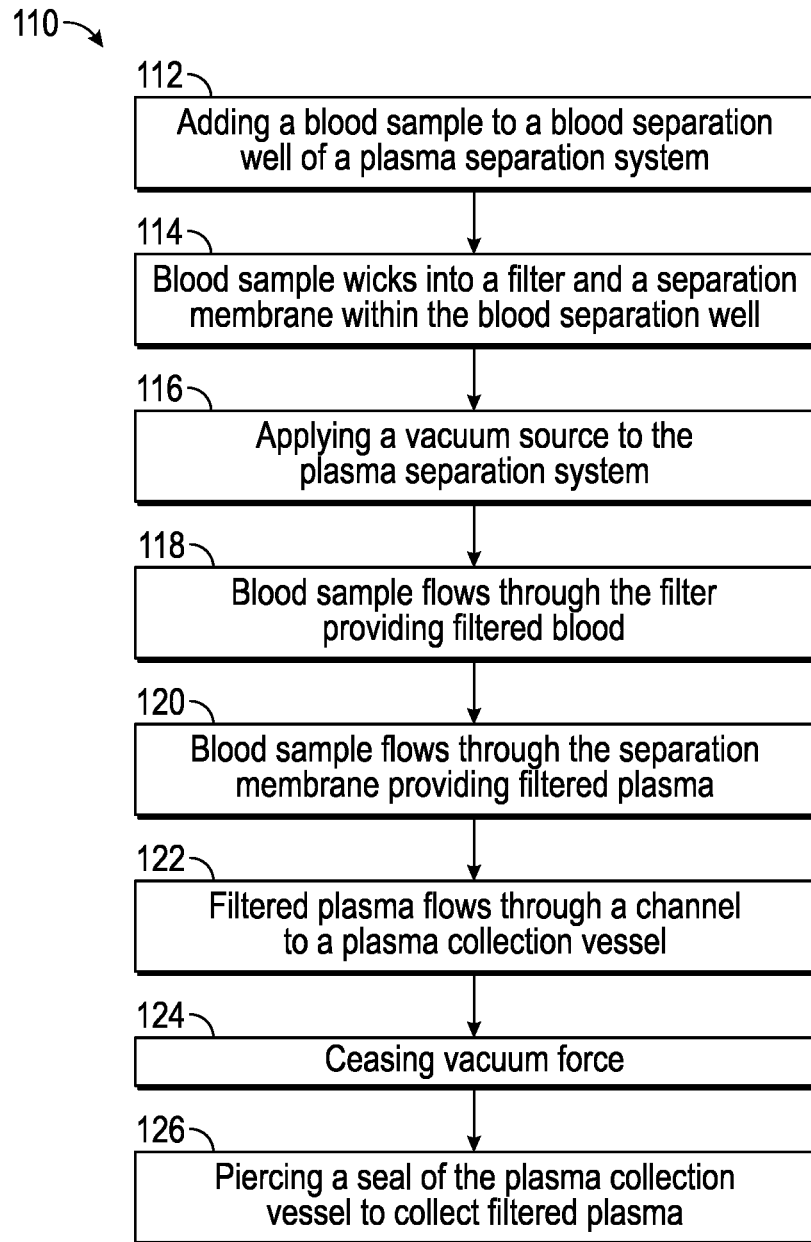
FIG. 6 is a flow chart of an exemplary method for separating filtered plasma from a blood sample in accordance with the present disclosure.

FIGS. 6 and 7A-7C illustrate an exemplary method for operating the plasma separator system 10 of FIG. 1. In particular, FIG. 6 illustrates a flow chart 110 for operating the plasma separation system 10.

Figure 7A:
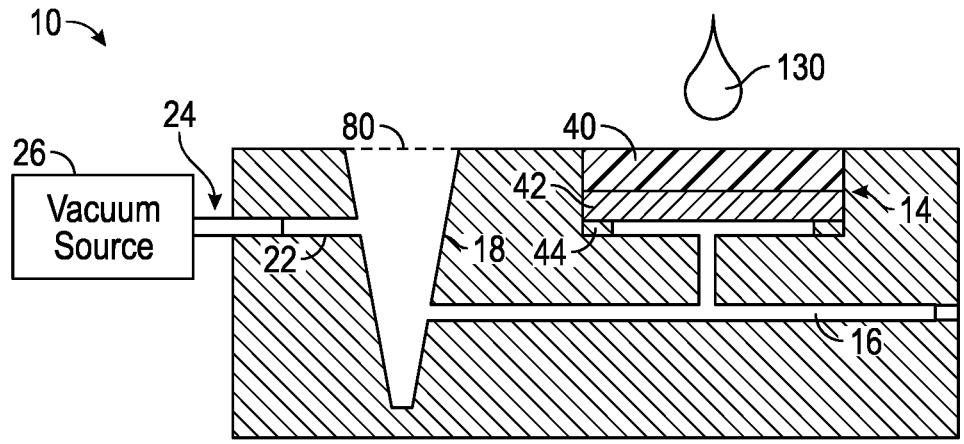
FIGS. 7A-7C collectively illustrate the use of an exemplary plasma separation system for separating filtered plasma from a blood sample in accordance with the method of FIG. 6.

To separate plasma from red and white blood cells in a blood sample, in a step 112, the blood sample 130 (e.g., 100 µl) may be added to the blood separation well 14 as illustrated in FIG. 7A. In some embodiments, a pipet, or other similar device, may be used to add the blood sample to the blood separation well 14.

In a step 114, the blood sample may wick into the filter 40 and the separation membrane 42. In some embodiments, the blood sample may be allowed to wick into the filter 40 and/or the separation membrane 42 for a pre-determined time period. For example, in one non-limiting example, the blood sample may be allowed to wick into the filter 40 and/or the separation membrane 42 for approximately 5-45 seconds.

In some embodiments, the blood sample may wick into the filter 40 and the separation membrane 42 by capillary action. In one non-limiting example, the presence of the one or more venting channels 68 (shown in FIG. 3) may promote wicking of the blood sample by providing escape of gas from edges of the filter 40 and/or the separation membrane 42. Further, the presence of microchannels 64 on the capillary surface 38 of the recess 30 may also promote capillary flow from the second side 56 of the separation membrane 42 into the channel 16 (shown in detail in FIG. 3).

Figure 7B:
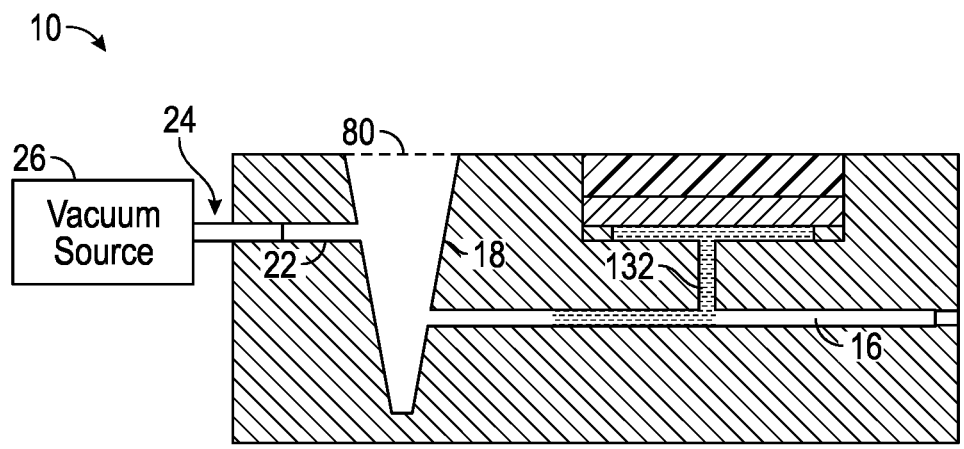

In a step 116, the negative pressure source 26 (e.g., vacuum source) may be actuated to apply the vacuum force to the blood separation well 14 via the outlet port 24. In a step 118, the vacuum force assists the blood sample to proceed through the filter 40 providing filtered blood. In a step 120, the blood sample may proceed through the separation membrane 42 providing filtered plasma 132 as illustrated in FIG. 7B. It should be noted that prior to application of vacuum source to the blood separation well 14, a portion of the blood sample may proceed through the filter 40 and/or the separation membrane 42.

Figure 7C:
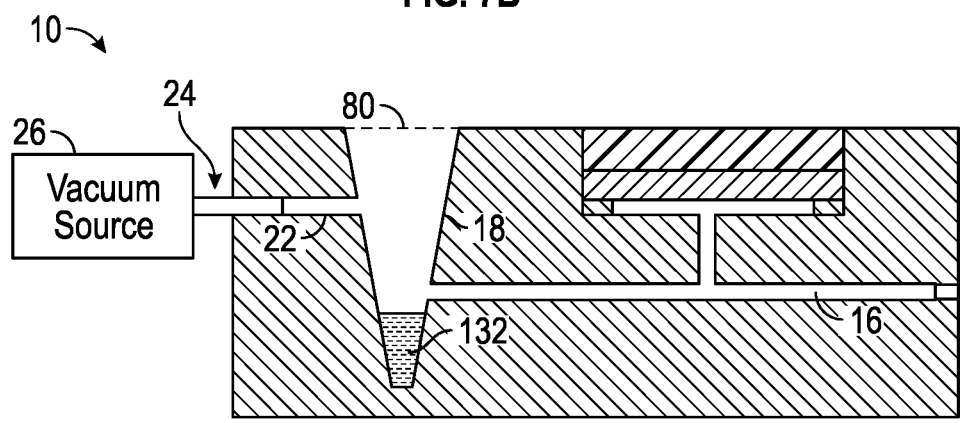

In a step 122, the filtered plasma 132 may flow through the channel 16 and collect in the plasma collection vessel 18 as illustrated in FIG. 7C. The vacuum force may be maintained at a substantially constant level until all needed filtered plasma is collected in the plasma collection vessel 18 or may increase over time to a set-point.

In a step 124, the vacuum force is caused to cease, such as by deactuating the negative pressure source 26 (e.g., vacuum source). In a step 126, the filtered plasma can be removed from the plasma collection vessel 18 such as by piercing the seal 80 of the plasma collection vessel 18. For example, a pipet tip may pierce the seal 80 and filtered plasma may be removed from the plasma collection vessel 18. One or more assay may then be performed using the filtered plasma. Quantitative and/or qualitative assays may be performed using the filtered plasma. For example, as the pipet may be capable of collecting a determinate amount of filtered plasma, quantitative assays may be performed.

In one example, a blood sample of 100 µL and 35% hematocrit (HCT) containing D-dimer at a concentration of 450 ng/ml may be added to the blood separation well 14 as illustrated in FIG. 7A. The filter 40 of the blood separation well 14 may be formed of VF2, and the separation membrane 42 may be formed of a polysulfone asymmetric membrane, for example. Using the process detailed in FIGS. 6 and 7, the blood sample may be allowed to wick into the filter 40 and/or separation membrane 42 for approximately 5-45 seconds. The negative pressure source 26 may be applied (e.g., between 0.05-2 psi) such that filtered plasma (e.g., approximately 20-25 µL) may be collected. The D-dimer concentration in the filtered plasma may then be measured (e.g., using a Siemens Stratus CS D-dimer immunoassay). In one example, the D-dimer concentration recovery for the filtered plasma, as compared to centrifugation was 100.8%.

In another example, a blood sample of 100 µL and 42% HCT containing TnI at a concentration of 100 pg/ml may be added to the blood separation well 14. Using the process detailed in FIGS. 6 and 7, the blood sample may be allowed to wick into the filter 40 and/or separation membrane 42 for approximately 5-45 seconds. The negative pressure source 26 may be applied (e.g., between 0.05-2 psi) such that filter plasma (e.g., approximately 20 µL) may be collected. The TnI concentration in the filtered plasma may then be measured (e.g., using Siemens Dimension EXL TnI immunoassay). In one example, the TnI concentration recovery for the filtered plasma, as compared to centrifugation was 86%.

Figure 8:
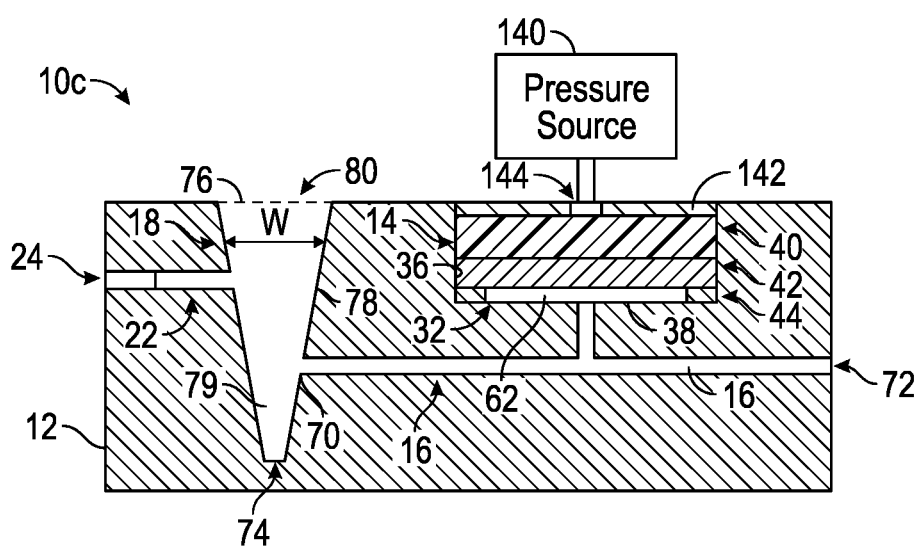
FIG. 8 is a cross-sectional view of another version of an exemplary plasma separation system having a pressure system connected to a blood separation well in accordance with the present disclosure

FIG. 8 illustrates another exemplary embodiment of a plasma separation system 10c. The plasma separation system 10c is similar to the plasma separation systems 10-10b illustrated in FIGS. 1, 4 and 5 respectively; however, the plasma separation system 10c applies positive force via a positive pressure source 140 upstream of the plasma collection vessel 18. In particular, the positive pressure source 140 may be connected to a cap 142 positioned over the filter 40 within the blood separation well 14.

In some embodiments, the cap 142 may be form fit over the filter 40 within the blood separation well 14. The cap 142 may include an outlet 144. The outlet 144 may connect to the positive pressure source 140. The positive pressure source 140 may provide between 0.05-2 psi of positive pressure to the blood separation well 14 during use. The positive pressure may force the blood sample through the filter 40, separation membrane 42, and/or channel 16 into the plasma collection vessel 18.

In some embodiments, the positive pressure source 140 may be a syringe loaded with air. By forcing air through the outlet 144, positive pressure may be applied to the blood sample forcing the blood sample through the filter 40, separation membrane 42, and/or channel 16 to the plasma collection vessel 18. In this embodiment, the outlet 24 downstream of the plasma collection vessel 18 may be used as a vent and opened as needed.

From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

The following is a list of non-limiting illustrative embodiments of the invention:

1. An apparatus, comprising:
a blood separation well for collection of a blood sample, the blood separation well having a recess intersecting a surface of the blood separation well; a separation membrane positioned on the surface of the recess for filtration of the blood sample to provide filtered plasma; a plasma collection vessel; a first channel connecting the blood separation well to the plasma collection vessel proximate to the surface of the recess; and, a second channel connecting the plasma collection vessel to a first outlet port, wherein the plasma collection vessel and the first channel are configured to convey a pressure force to provide filtered plasma to the plasma collection vessel.

2. The apparatus of illustrative embodiment 1, wherein the pressure force is a negative pressure force and the first channel, the plasma collection vessel, and the second channel are configured to convey the negative pressure force applied to the first outlet port to the surface of the recess.

3. The apparatus of illustrative embodiments 1 or 2, further comprising a cap positioned on the separation membrane, the cap having a second outlet port formed therein, wherein the pressure is a positive pressure force and the first channel is configured to convey the positive pressure force applied through the second outlet port to the plasma collection vessel.

4. The apparatus of any one of illustrative embodiments 1-3, further comprising a filter positioned within the recess and on the separation membrane, the filter having a plurality of structures surrounding pores configured to separate red blood cells from the blood sample to provide filtered blood, the filtered blood having a reduction in red blood cells as compared to an amount of red blood cells in the blood sample.

5. The apparatus of illustrative embodiment 4, wherein at least one of the separation membrane or filter is coated with a blocking agent.

6. The apparatus of illustrative embodiment 4, wherein at least one of the separation membrane or filter is treated with a surfactant.

7. The apparatus of illustrative embodiment 4, further comprising a cap positioned at a surface of the housing for containing the separation membrane and filter within the recess.

8. The apparatus of illustrative embodiment 7, wherein the cap includes at least one venting hole.

9. The apparatus of any one of illustrative embodiments 1-8, wherein the surface is defined further as a capillary surface having at least one microchannel.

10. The apparatus of illustrative embodiment 9, wherein capillary surface has a plurality of microchannels forming a concentric pattern in the capillary surface, the concentric pattern having a set of radial microchannels projecting from a location.

11. The apparatus of any one of illustrative embodiments 1-10, further comprising a vacuum source connected to the second channel at the outlet port.

12. The apparatus of illustrative embodiment 11, wherein the vacuum source is a syringe pump, the syringe pump providing a vacuum force between 0.05 psi and 2 psi.

13. The apparatus of any one of illustrative embodiments 1-13, wherein the plasma collection vessel is a serpentine channel.

14. The apparatus of any one of illustrative embodiments 1-13, wherein the plasma collection vessel has a proximal end and a distal end, the distal end positioned at a surface of the housing and wherein the plasma collection vessel includes a seal configured to be pierced by a pipette.

15. The apparatus of illustrative embodiment 14, wherein the first channel is connected to the plasma collection vessel at the proximal end of the plasma collection vessel.

16. The apparatus of any one of illustrative embodiments 1-15, wherein the blood separation well further comprises at least one vent positioned in the recess of the blood separation well, the vent positioned beyond an outer edge of the separation membrane.

17. The apparatus of any one of illustrative embodiments 1-16, further comprising an adhesive member connecting the surface and the separation membrane within the recess.

18. The apparatus of any one of illustrative embodiments 1-17, wherein the separation membrane is an asymmetric membrane having a first set of pores larger than a second set of pores, the first set of pores located on a first side of the separation membrane and the second set of pores located on a second side of the separation membrane.

19. The apparatus of any one of illustrative embodiments 1-18, wherein the separation membrane is pressure fit within the recess of the blood separation well.

20. The apparatus of any one of illustrative embodiments 1-19, wherein the plasma collection vessel is conically shaped and has capacity to collect at least 20 μL of filtered plasma.

21. The apparatus of any one of illustrative embodiments 1-20, further comprising a housing having a surface, wherein the recess of the blood separation well intersects the surface of the housing and the surface of the blood separation well.

22. A kit comprising: a plasma separation system comprising: a housing having a surface; a blood separation well for collection and filtration of a blood sample to provide filtered plasma, the blood separation well having a recess intersecting the surface of the housing and a surface of the blood separation well;
an adhesive member positionable on the surface of the recess; a separation membrane configured to adhere to the adhesive member; and; a filter positionable on the separation membrane and pressure fit within the recess; a plasma collection vessel; a first channel connecting the surface of the blood separation well to the plasma collection vessel; a second channel connecting the plasma collection vessel to an outlet port; and, a vacuum source configured to connect to the outlet port, the vacuum source configured to provide between 0.05 psi and 2 psi vacuum force to the outlet port.

23. A method comprising: providing a blood sample to a plasma separation system, the plasma separation system comprising: a blood separation well containing a filter and a separation membrane, the blood separation well connected to a plasma collection vessel by a first channel, and the plasma collection vessel connected to a second channel with an outlet port, the outlet port connected to a vacuum source; wherein the blood sample wicks into the filter for a first pre-determined time interval; and, actuating the vacuum source to apply a vacuum source to the blood separation well via the outlet port to enhance flow of plasma from the blood sample through the filter and separation membrane providing filtered plasma, and to draw the filtered plasma through the first channel into the plasma collection vessel.

24. The method of illustrative embodiment 23, wherein the plasma collection vessel includes a seal; the method further comprising: piercing, with a pipette, the seal of the plasma collection vessel; and, collecting filtered plasma with the pipette.

What is claimed is:

1. A kit comprising:
a plasma separation system comprising:
a housing having a first surface;
a blood separation well formed at the first surface of the housing for collection and filtration of a blood sample to provide filtered plasma, the blood separation well having a recess intersecting a second surface of the housing within the blood separation well;
an adhesive member positionable on the second surface of the housing within the blood separation well;
a separation membrane configured to adhere to the adhesive member;
a filter positionable on the separation membrane;
a plasma collection vessel within the housing, the plasma collection vessel having a proximal end and a distal end;
a first channel extending within the housing and connecting the blood separation well to the plasma collection vessel;
a second channel connecting the plasma collection vessel to an outlet port; and,
a vacuum source configured to connect to the outlet port, the vacuum source configured to provide between 0.05 psi and 2 psi vacuum force to the outlet port.

2. The kit of claim 1, wherein the first channel, the plasma collection vessel, and the second channel are configured to convey the vacuum force applied to the outlet port to the recess.

3. The kit of claim 1, further comprising a cap positioned on the separation membrane, the cap having a second outlet port formed therein, wherein the first channel is configured to convey a positive pressure force applied through the second outlet port to the plasma collection vessel.

4. The kit of claim 1, wherein the filter has a plurality of structures surrounding pores configured to separate red blood cells from the blood sample to provide filtered blood, the filtered blood having a reduction in red blood cells as compared to an amount of red blood cells in the blood sample.

5. The kit of claim 4, wherein at least one of the separation membrane or filter is coated with a blocking agent.

6. The kit of claim 4, wherein at least one of the separation membrane or filter is treated with a surfactant.

7. The kit of claim 1, wherein the second surface is defined further as a capillary surface having at least one microchannel.

8. The kit of claim 7, wherein the capillary surface has a plurality of microchannels forming a concentric pattern in the capillary surface, the concentric pattern having a set of radial microchannels projecting from a location.

9. The kit of claim 1, wherein the vacuum source is a syringe pump.

10. The kit of claim 1, wherein the first channel is connected to the plasma collection vessel at the proximal end of the plasma collection vessel.

11. The kit of claim 1, wherein the blood separation well further comprises at least one vent positioned in the recess of the blood separation well, the vent positioned beyond an outer edge of the separation membrane.

12. The kit of claim 1, wherein the separation membrane is an asymmetric membrane having a first set of pores larger than a second set of pores, the first set of pores located on a first side of the separation membrane and the second set of pores located on a second side of the separation membrane.

13. The kit of claim 1, wherein the housing is a unitary integral device that is shaped to form the blood separation well, the plasma collection vessel, the first channel, and the second channel.

14. The kit of claim 1, wherein the first channel intersects the plasma collection vessel a distance away from the distal end of the plasma collection vessel.

15. The kit of claim 1, wherein the first channel intersects the plasma collection vessel between the proximal end and the distal end.

16. The kit of claim 1, wherein the first channel intersects the proximal end of the plasma collection vessel.

* * * * *